(12) United States Patent
Seeley et al.

(10) Patent No.: US 9,707,338 B2
(45) Date of Patent: Jul. 18, 2017

(54) PERSONALIZED HOUSING FOR AMBULATORY INFUSION DEVICE

(71) Applicant: MEDTRONIC, INC., Minneapolis, MN (US)

(72) Inventors: Dale F. Seeley, Spring Park, MN (US); Michael C. Schmitz, Prior Lake, MN (US); Keith R. Hildebrand, Houlton, WI (US); Edwin Rivera, Ham Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/063,870

(22) Filed: Oct. 25, 2013

(65) Prior Publication Data

US 2015/0119804 A1    Apr. 30, 2015

(51) Int. Cl.
    *A61M 5/14*     (2006.01)
    *A61M 5/142*    (2006.01)
    *A61M 5/168*    (2006.01)

(52) U.S. Cl.
    CPC ...... *A61M 5/14248* (2013.01); *A61M 5/1413* (2013.01); *A61M 5/16877* (2013.01); *A61M 2005/14252* (2013.01); *A61M 2005/14268* (2013.01); *A61M 2205/581* (2013.01); *A61M 2205/583* (2013.01); *A61M 2205/584* (2013.01); *A61M 2205/586* (2013.01); *A61M 2205/59* (2013.01)

(58) Field of Classification Search
    CPC ........ A61M 5/1413; A61M 2205/3553; A61M 2205/3569; A61M 2205/3584; A61M 2205/3592; A61M 2205/52; A61M 2230/201; A61M 5/142; A61M 5/14244; A61M 5/172; A61M 5/1723; A61M 2005/14268; A61M 2205/505; A61M 5/14248; A61M 5/16804
    See application file for complete search history.

(56) References Cited

U.S. PATENT DOCUMENTS

| | | |
|---|---|---|
| 7,303,543 B1 | 12/2007 | Maule |
| 7,713,240 B2 | 5/2010 | Istoc |
| 2008/0051727 A1* | 2/2008 | Moberg et al. ............... 604/207 |
| 2011/0054285 A1 | 3/2011 | Searle |
| 2012/0053522 A1 | 3/2012 | Yodfat |

(Continued)

*Primary Examiner* — Imani Hayman
(74) *Attorney, Agent, or Firm* — Mueting, Raasch & Gebhardt, P.A.

(57) ABSTRACT

An ambulatory infusion device includes a common module having a pump mechanism and a fluid flow path in communication with the pump mechanism. The device also includes a custom module operably coupleable to the common module. The custom module includes a reservoir for housing a liquid composition comprising a medicament and control electronics. The reservoir is configured to fluidly couple with the fluid flow path, and the control electronics are configured to electrically couple to the pump mechanism when the common module and the custom module are operably coupled. When the common module and the custom module are operably coupled, the pump mechanism is configured to drive the liquid composition from the reservoir to a patient via the fluid flow path, and the control electronics are configured to control the rate at which the pump mechanism drives the liquid composition.

20 Claims, 8 Drawing Sheets

(56) References Cited

U.S. PATENT DOCUMENTS

2012/0184907 A1* 7/2012 Smith et al. .................. 604/152
2014/0213976 A1* 7/2014 Bitton ................... A61M 5/003
                                                        604/151

* cited by examiner

PERSONALIZED HOUSING FOR AMBULATORY INFUSION DEVICE

FIELD

This disclosure generally relates to, among other things, medical infusion devices, particularly to modular ambulatory infusion devices having a housing component containing control electronic elements for personalized therapy.

BACKGROUND

Ambulatory infusion devices have been developed for treatment of specific diseases, such as diabetes. Accordingly, the ability to modify an ambulatory infusion device configured to deliver a particular therapy, such as insulin for diabetes treatment, for another therapy, such as ropinirole for treatment of Parkinson's disease, can be challenging. Design architectures for ambulatory infusion devices have generally included a durable (reusable) portion and consumable (disposable) portion that are tailored to particular therapies and patient needs. Modification of such therapy-specific ambulatory infusion devices to accommodate different therapies or patient needs would typically require a completely new design since the architecture must change.

SUMMARY

This disclosure describes, among other things, ambulatory infusion device platforms that combine common features into one or more modules and custom features into one or more other modules so that the platform may be used across a variety of therapies by changing the custom module. The shift in architecture from durable and consumable parts to common and custom units provides greater flexibility to meet a greater variety of therapy and patient needs. Preferably, the common module includes a standard pump mechanism and other features that are common between different therapies and users. The common module, or portions of the common module, may be disposable, while the custom module, or portions of the custom module, is preferably reusable. The custom module includes control electronics and a reservoir component for housing a liquid composition comprising a medicament. The common module and control module are configured such that the reservoir component and the control electronics are operably coupleable to the pump mechanism. The control electronics are configured to control the rate at which the pump mechanism causes the liquid composition from the reservoir to be delivered to the patient.

In addition to customizable therapy through choice of medicament and delivery rate control via control electronics, the custom module may have a form factor tailored to the patient or the therapy being delivered. By way of example, patients suffering from movement disorders may not be able to readily handle smaller units and may prefer the custom unit to be larger than the custom unit for a patient having a good deal of dexterity, who may prefer a smaller custom unit for purposes of comfort or discreetness. In addition to size, shape may be customized to accommodate a particular patient's needs or desires. Further, as ambulatory devices, such as patch pump devices, are typically worn by a patient and thus visible to the patient or others, the custom unit may include other design features selected by the patient, such as color, image, pattern, or the like.

In embodiments disclosed herein, an ambulatory infusion device includes a common module comprising a pump mechanism and a fluid flow path in communication with the pump mechanism. The infusion device also includes a custom module operably coupleable to the common module. The custom module includes a reservoir for housing a liquid composition comprising a medicament and control electronics. The reservoir is configured to fluidly couple with the fluid flow path, and the control electronics are configured to electrically couple to the pump mechanism when the common module and the custom module are operably coupled. When the common module and the custom module are operably coupled, the pump mechanism is configured to cause the liquid composition from the reservoir to be delivered to a patient via the fluid flow path. The control electronics are configured to control the rate at which the pump mechanism causes the liquid composition to be delivered.

In embodiments disclosed herein, a custom module for an ambulatory infusion device assembly includes a housing configured to releasably engage with a common module of the ambulatory device assembly. The common module includes a pump mechanism and a fluid flow path in communication with the pump mechanism. The custom module further includes control electronics disposed within the housing. The control electronics include an interconnect configured to electrically couple with an interconnect of the common module when the housing is engaged with the common module. The interconnect of the common module is electrically coupled to the pump mechanism of the common module. The control electronics are electrically coupled to the pump mechanism when the housing is engaged with the common module and are configured to control the operation rate of the pump mechanism. The custom module also includes a reservoir component disposed within the housing. The reservoir component includes a reservoir fluidly coupled with a fluid interconnect. The fluid interconnect is configured to fluidly couple with the fluid flow path of the common module when the housing is engaged with the common module.

One or more embodiments of the devices, systems or methods described herein provide one or more advantages over prior devices, systems or methods. As indicated above, the ambulatory infusion devices described herein provide for a platform that can be used across a variety of therapies and with a variety of patient populations. In embodiments, the ambulatory infusion devices have a common module that includes a standard pump mechanism and other features that are common between different therapies and users. The devices also include a custom module that includes patient or therapy-selective components such as control electronics for controlling operation rate of the pump mechanism and a reservoir for housing a liquid composition comprising a medicament. Thus, patient or therapy-selective parameters such as medicament and infusion rate are present or controlled by the custom module, while common components such as the pump mechanism are included in the common module. Production of such a flexible system that can be used across a variety of therapies and with a variety of patient populations may enable a broader array of therapies to be delivered by an ambulatory infusion device. This and other advantages will be readily understood from the following detailed description.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, apparatuses, systems and methods are disclosed. It is to be understood that other embodiments are contemplated and may be made without departing from the scope or spirit of the present disclosure. The following detailed description, therefore, is not to be taken in a limiting sense.

This disclosure generally relates to, inter alia, ambulatory infusion devices, such as patch pumps, having a common module and a personalized therapy selective custom module. In embodiments, the common module includes a standard pump mechanism and other features that are common between different therapies and users. The common module, or portions of the common module, may be disposable, while the custom module, or portions thereof, is preferably reusable. The custom module includes therapy or patient selective components such as (i) control electronics configured to control operation rate of the pump mechanism of the common module when operably coupled, and (ii) a reservoir component for housing a liquid composition comprising a medicament. Thus, patient- or therapy-selective parameters such as medicament and infusion rate are present or controlled by the custom module, while common components such as the pump mechanism are included in the common module. Production of such a flexible system that can be used across a variety of therapies and with a variety of patient populations may enable a broader array of therapies to be delivered by ambulatory infusion device.

The custom modules and common modules described herein may together form any suitable ambulatory infusion device. As used herein, "ambulatory", with regard to an infusion device, means that the infusion device is wearable or attachable to a patient such that the patient can readily move about while wearing the device or while the device is attached to the patient. Ambulatory pumps may be configured to deliver medicaments transdermally, transcutaneously, subcutaneously or the like. Ambulatory pumps include patch pumps that are configured to adhere to a patient's skin. Examples of ambulatory pumps include Medtronic MiniMed's PARADIGM insulin pumps, Animas Corporation's VIBE and ONE TOUCH PING insulin pumps, Insulet Corporation's OMNIPOD system, Roche Insulin Delivery Systems Inc.'s ACCU-CHEK COMBO system, and Tandem Diabetes Care's TSLIM insulin pump. One example of a patch pump is described in U.S. Pat. No. 8,025,658 entitled "ADHESIVE PATCH SYSTEMS AND METHODS" issued on Sep. 27, 2011, which patent is hereby incorporated herein by reference in its entirety to the extent that it does not conflict with the present disclosure. The devices and systems described above may be readily modified to employ custom modules and common modules described herein and may be used to deliver any suitable medicament for any suitable therapeutic purpose.

Figure 1:
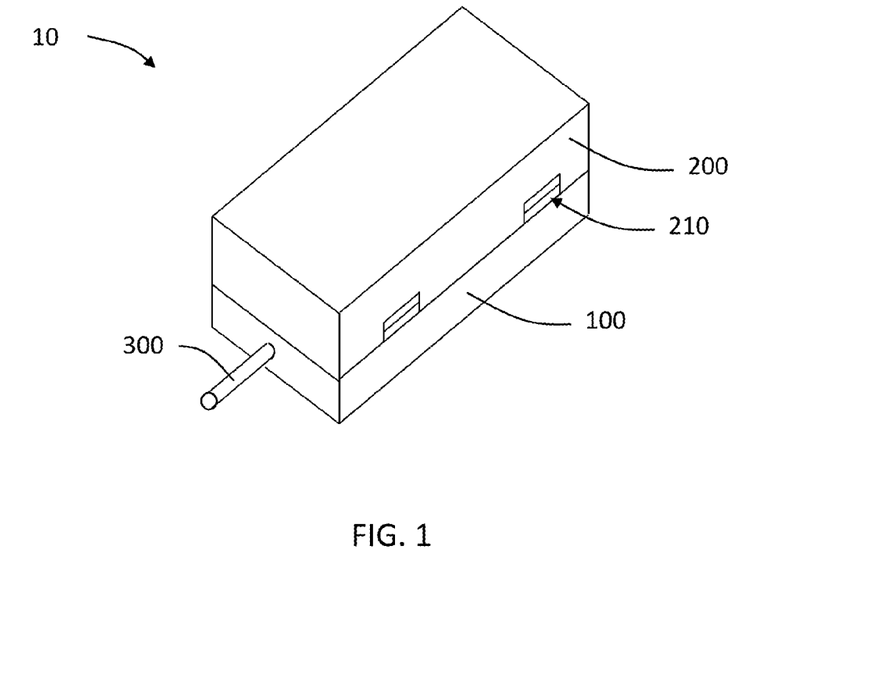
FIGS. 1-2 are schematic perspective views of embodiments of ambulatory infusion devices.
Figure 2:
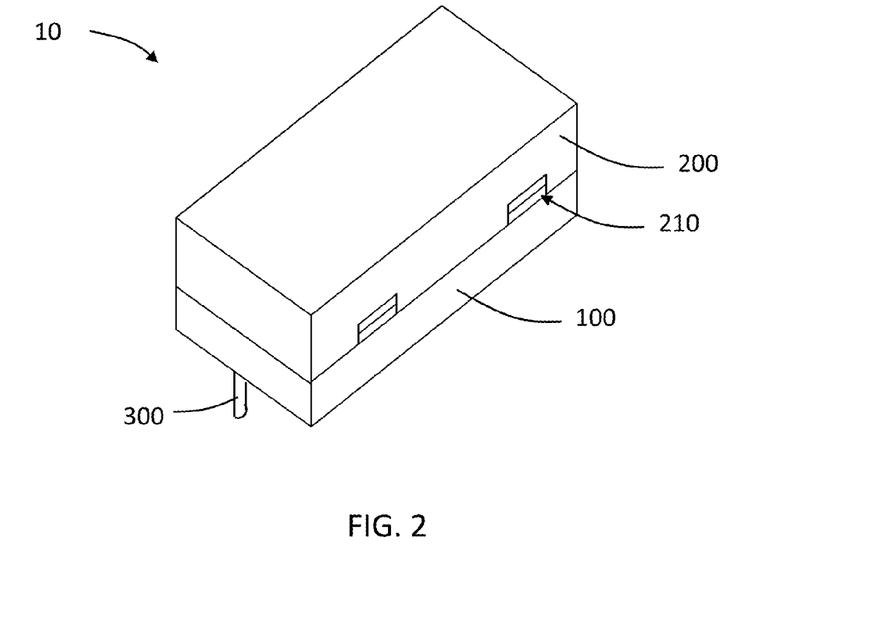

Referring now to FIGS. 1-2, schematic drawings of embodiments of ambulatory infusion devices 10 are shown. The infusion devices 10 include a common module 100 and a custom module 200. The common module 100 and the custom module 200 include cooperating engagement elements 210 to releasably secure the common module 100 relative to the custom module 200. The engagement elements 210 may cooperate in any suitable manner to releasably secure the common module 100 to the custom module 200. For example, the custom module may be secured to the common module by sliding the custom module on the common module. Alternatively, the custom module may be secured to the common module by parts, such as sliding parts that mate. By way of further example, the custom module may be secured to the common module by snapping parts that mate. By way of yet another example, the custom module may be secured to the common module by screwing the custom module on the common module through interaction of cooperating threads. Still another example includes use of magnets to secure the custom module to the common module. It will be understood that these are but a few example of the ways in which the custom module may be secured to the common module and that many other ways are possible and are contemplated herein.

Still with reference to FIGS. 1-2, the infusion devices 10 include an outlet 300 for delivering a liquid composition comprising a medicament to the patient. In the embodiment depicted in FIG. 1, the outlet 300 comprises a tube or cannula for connection with an infusion set, which may, for example, be attached to a patient's skin. In the embodiment depicted in FIG. 2, the outlet 300 comprises a cannula for transdermally delivering a liquid composition comprising a medicament to a patient, such as to a subcutaneous space of the patient. The infusion device 10 depicted in FIG. 2 may be a patch pump that would include an adhesive layer (not shown) between the common module 100 and the patient's skin (or as a part of the common module) for adhering the infusion device 10 to the patient.

Figure 3:
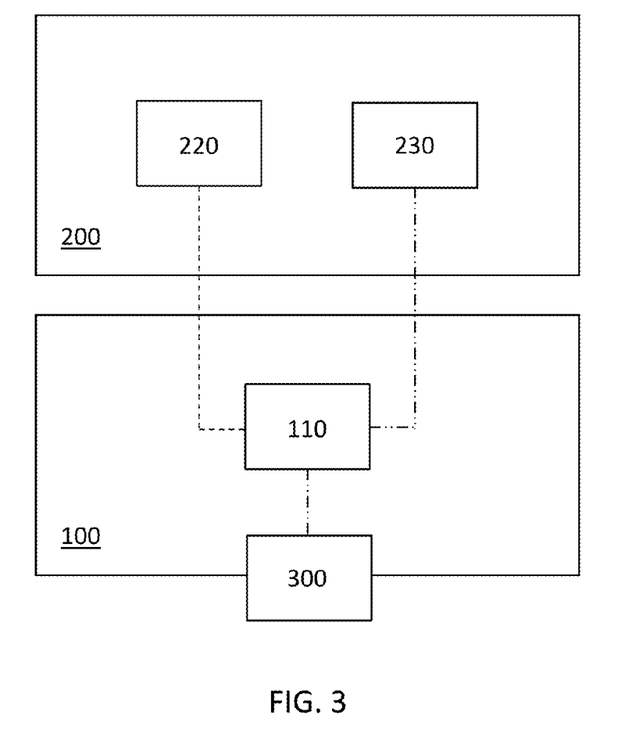
FIG. 3 is a schematic block diagram showing select components of an embodiment of an ambulatory infusion device.

Referring now to FIG. 3, a schematic block diagram of a selected component of an ambulatory infusion device is shown. The device includes a custom module 200 that includes control electronics 220 and a reservoir 230. The device further includes a common module 100 configured to releasably secure to the custom module 200. The common module includes a pump mechanism 110 and an outlet 300 in fluid communication with a fluid path of the pump mechanism 110. When the common module 100 is operably coupled to the custom module 200, the reservoir 230 is fluidly coupled to the flow path of the pump mechanism 110, and the control electronics 220 are operably coupled to the pump mechanism 110. The control electronics 220 are configured to control the rate at which the pump mechanism 110 causes (e.g., drives or releases) a liquid composition comprising a medicament from the reservoir 230 to exit the outlet 300. Control electronics 220 may include components that provide for changing volume of alarms, switching between preset delivery rates, or other features that are directed to a particular therapy, patient population, or patient.

Control electronics 220 may include a processor, memory, user interface, timer, clock or counter, power source, interconnect, sensors or the like. Control electronics 220 may include any suitable processor, such as one or more microprocessors, DSPs, ASICs, FPGAs, programmable logic circuitry, or the like, and the functions attributed to the processor herein may be embodied as hardware, firmware, software or any combination thereof. Memory may store instructions that cause processor to provide the functionality ascribed to a system or device described herein, and may store information used by processor to provide the functionality ascribed to a system or device described herein. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A power source may deliver operating power to components of a system or apparatus described herein. Power source may be an AC or DC power source, such as a battery and a power generation circuit to produce the operating power.

Methods described in this disclosure, including those attributed to devices or systems, or various constituent components, may be implemented, at least in part, in hardware, software, firmware or any combination thereof. For example, various aspects of the methods may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices.

When implemented in software, the functionality ascribed to the systems, apparatuses and methods described in this disclosure may be embodied as instructions on a computer-readable medium such as RAM, ROM, NVRAM, EEPROM, FLASH memory, magnetic data storage media, optical data storage media, or the like. Such computer-readable medium is non-transitory. The instructions may be executed by one or more processors to support one or more aspects of the functionality described in this disclosure.

Pump mechanism 110 may include any suitable mechanism to drive or release fluid from the reservoir 230 to the outlet 300. For example, the drive mechanism may be pressurized gas, drive syringe or piston, electrolytic, or the like.

Figure 4:
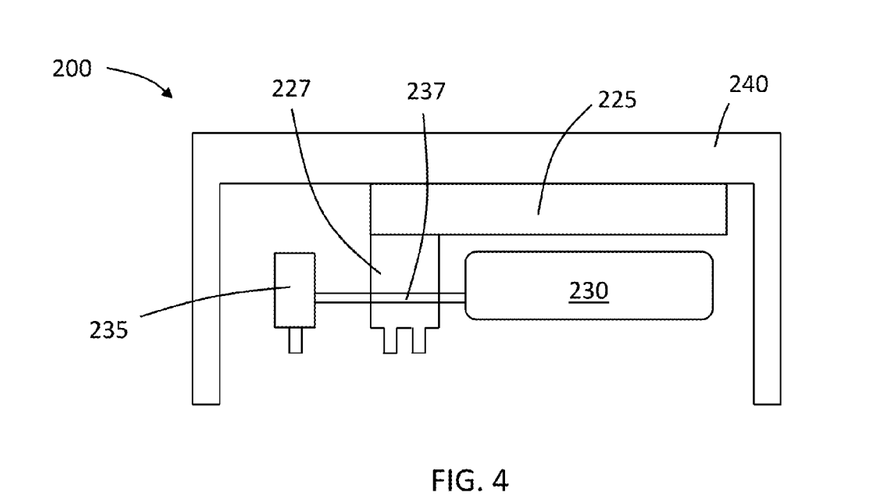
FIG. 4 is a schematic cross sectional diagram showing some components of an embodiment of a custom module of an ambulatory infusion device.

Referring now to FIG. 4, a schematic cross sectional drawing showing some components of a custom module 200 is shown. The custom module comprises a housing 240. Housing 240 may be formed of any suitable material or combination of materials. Suitable materials include metal, alloys and polymers. Disposed in the housing are a circuit board 225 and an electrical interconnect 227 operably coupled to the circuit board 225 as part of the control electronics. The circuit board 225 may be mounted or attached to the housing 240. Custom module 200 also includes a reservoir assembly that includes reservoir 230, fluid flow path component 237 in communication with reservoir 230, and fluid interconnect 235 in communication with the fluid flow path component 237. The reservoir 230 or other fluid components may be releasably securable to housing; e.g., through interference fit, snap fit, or the like. Any suitable reservoir may be employed. For example, the reservoir may be a pressurized bellows-type reservoir, unpressurized bellows-type reservoir, elastomeric reservoir, thin film polymer or metal reservoir, or the like. In embodiments, the reservoir is a prefilled reservoir, such as a prefilled reservoir disclosed in U.S. patent application 14/063,883 entitled PREFILLED RESERVOIR APPARATUS FOR AMBULATORY INFUSION DEVICE, filed on the same day as the present application and naming Michael Schmitz, Keith Hildebrand, and Dale Seeley as inventors, which patent application is hereby incorporated herein by reference in its entirety to the extent that it does not conflict with the disclosure presented herein.

It will be understood that the custom module 100 may include other components that are not depicted in FIG. 4. By way of example, the custom module may include a power supply as part of the control electronics.

Figure 5:
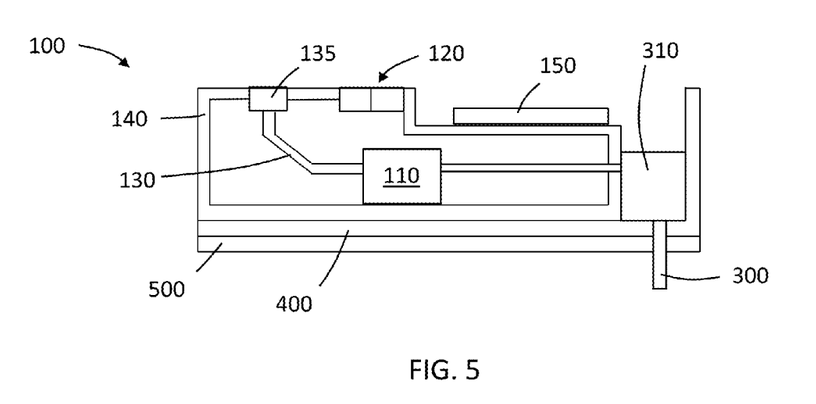
FIG. 5 is a schematic cross sectional diagram showing some components of an embodiment of a common module of an ambulatory infusion device.

Referring now to FIG. 5, a schematic cross sectional drawing showing some components of a common module 100 is shown. In the depicted embodiment, the common module 100 includes an adhesive layer 500 for securing the common module to skin of a patient. The adhesive layer 500 is disposed on plate 400, which is releasably coupleable to housing 140. Pump mechanism 110 is disposed in housing 140 and is in communication with fluid flow path components 130 that fluidly couple pump mechanism 110 to fluid interconnect 135 and fluid interconnect 310, which is fluidly coupled to outlet cannula 300. Pump mechanism 110 is operably coupled to electrical interconnect 120. In the depicted embodiment, the common module 100 includes a circuit board 150 as part of control electronics. A processor, memory or the like may be coupled to a circuit board to allow control electronics for common pump and sensing controls. For example, control electronics of the common module may be configured to detect device malfunctions such as occlusions or leaks in the fluid flow path through the use of appropriate pressure sensors (not shown), may control or assist in control in the rate at which therapeutic agent is delivered, or the like.

It will be understood that the common module 100 may include other components that are not depicted in FIG. 5. By way of example, the common module may include a power supply as part of the control electronics.

In some embodiments, both custom module and common module include a power supply. In other embodiments, only one of the custom module and the common module includes a power supply and power may be shared when the common module and the custom module are operably coupled through interconnects (e.g., interconnect 135 of common module depicted in FIG. 5 and interconnect 235 of custom module depicted in FIG. 4).

Figure 6:
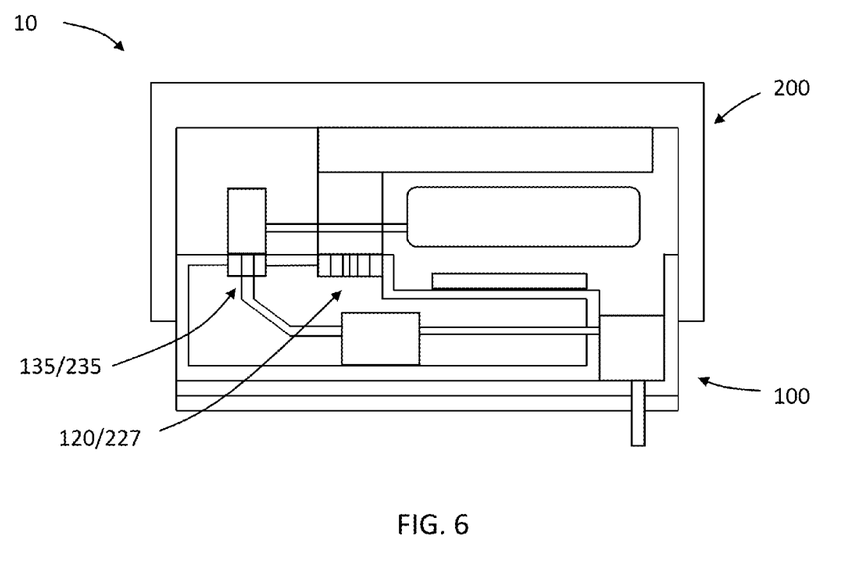
FIG. 6 is a schematic cross sectional diagram showing the custom module of FIG. 4 operably coupled to the common module of FIG. 5.

Referring now to FIG. 6, a schematic cross sectional diagram of the custom module 200 depicted in FIG. 4 and the common module 100 depicted in FIG. 5 are shown in operably coupled configuration. Not all of the depicted components are listed, as the components are listed and discussed above with regard to FIGS. 4-5. Highlighted are connection of electrical interconnects 120 and 227 and fluid interconnects 135 and 235 when the common module 100 and custom module 200 are operably coupled. Any suitable fluid interconnect may be employed, such as needle and self-sealing septum or the like.

Figure 7:
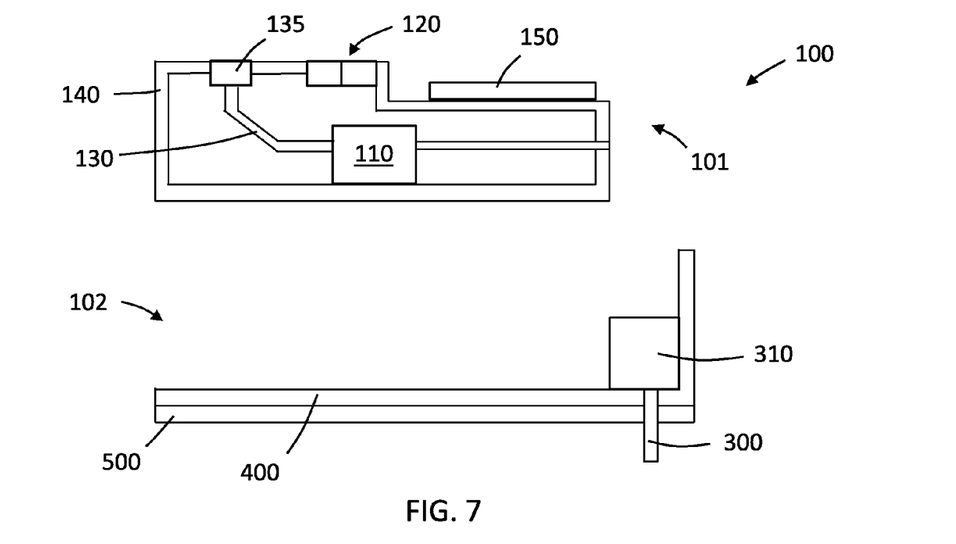
FIG. 7 is a schematic cross sectional diagram of the common module of FIG. 5 showing disposable components separated from reusable components.

Referring now to FIG. 7, components of the common module depicted in FIGS. 5-6 are shown separated. The separated components include component 102 that may be disposable and component 101 that may be reusable. Component 102 includes adhesive layer 500, plate 400, fluid interconnect 310 and cannula 300. It may be desirable to dispose of component 102 when the infusion apparatus is moved to a different location of the patient.

Ambulatory patch pumps, of which the common module 100 depicted in FIG. 7 is a part, require periodic movement of a cannula 300 that is punctured through a patient's skin to avoid dermatological or immunological complications or infections. Often, the cannula is moved every three days. It is generally not recommended to reuse a cannula. Accordingly, placing cannula 300 and associated fluid coupling components 310 on a disposable component 102 may be desirable. In addition, adhesive layer 500 tends to be ineffective after removal from a patient's skin. Accordingly, when the patch pump is moved to a new location, component 102 may be replaced with a new component 102. Component 101, which includes reusable components that may be of relatively high cost, may be reused and releasable attached to new component 102 when the location of the pump is changed.

Component 101 includes housing 140, fluid flow path 130, pump mechanism 110, fluid interconnect 135, electrical interconnect 120, and circuit board 150. Of course, other reusable components that are not depicted may be included in reusable component 101 of common module 100.

Figure 8:
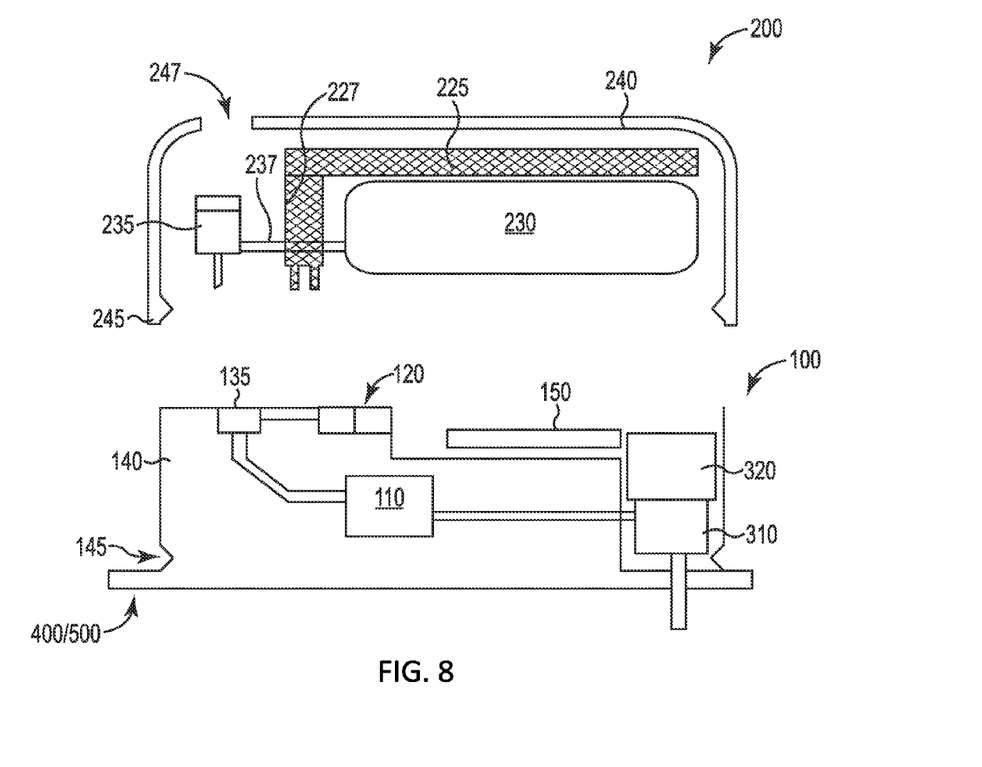
FIG. 8 is a schematic cross sectional diagram showing some components of an embodiment of an ambulatory infusion device.

Referring now to FIG. 8, a schematic cross section of an embodiment of a patch pump is shown. Many of the components depicted in FIG. 8 are depicted in, and discussed with regard to, FIGS. 4-7. To the extent that components depicted in FIG. 8 are not discussed with regard to FIG. 8, reference is made to the discussion above regarding FIGS. 4-7. As shown in FIG. 8, housing 240 of custom module 200 includes securing elements 245 (detents in the depicted embodiment) for cooperating with complementary securing features 145 (indents in the depicted embodiment) of housing 140 of common module 100. The securing elements 245 and securing features 145 cooperate to releasable secure custom module 200 to common module 100.

The common module 100 in FIG. 8 includes a mechanism 320 for inserting cannula 300 into skin of a patient. Any suitable needle or cannula insertion mechanism may be employed, such as those employed with the variety of specific ambulatory devices listed above. For example, a needle or cannula insertion mechanism described in U.S. Pat. No. 8,025,658 may be employed.

Proper alignment of the custom module 200 and the common module 100 or other modules are desirably achieved to ensure proper fluid and electrical connection between components of each module. Proper alignment may be achieved and verified in any suitable manner. Preferably, sensory feedback is provided to a user to verify proper alignment or to indicate improper alignment.

Figure 9A:
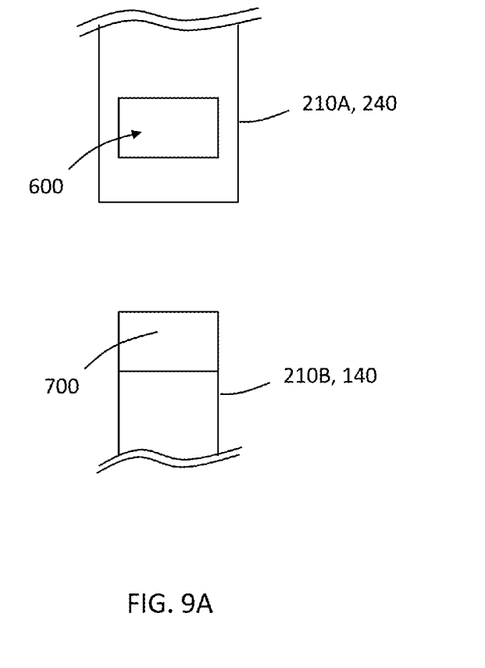
FIGS. 9A-D are schematic drawings showing releasably interlocking elements of a common module and a custom module: A and C; front views, B and D, side views; A and B, not interlocked; C and D, interlocked.
Figure 9B:
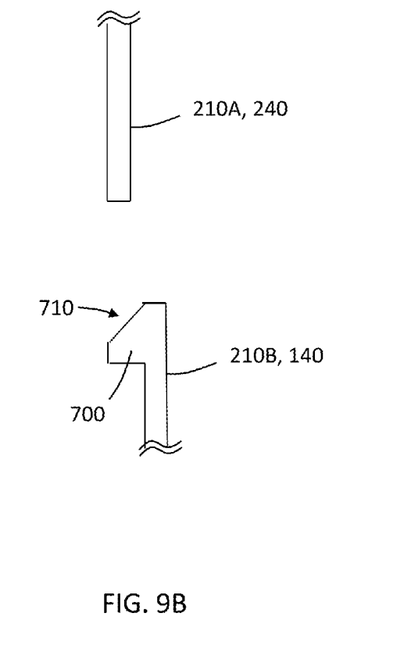
Figure 9C:
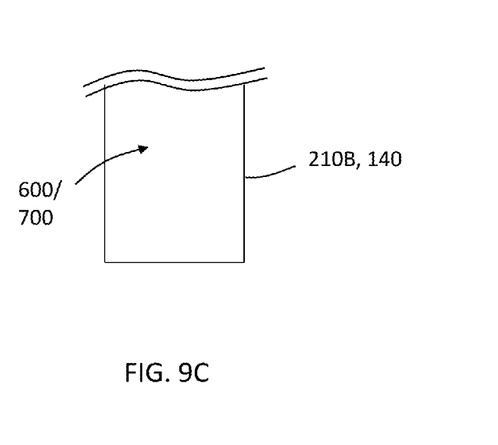
Figure 9D:
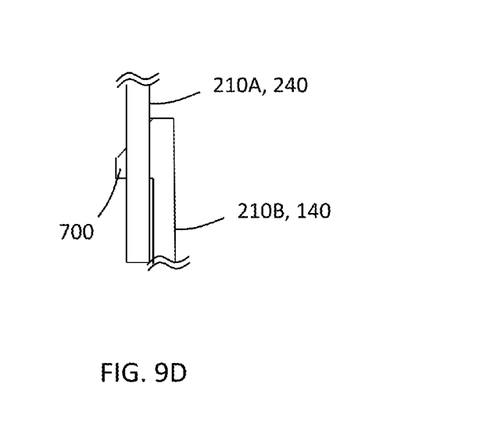
Figure 10A:
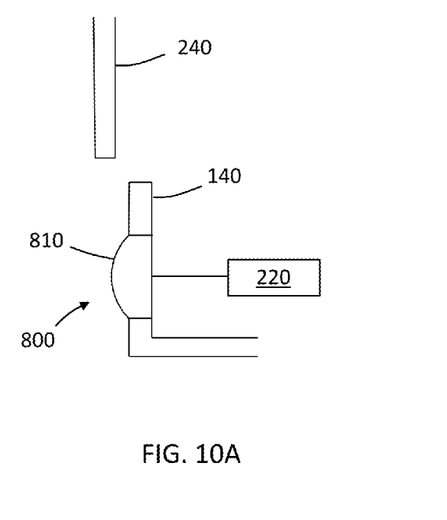
FIGS. 10A-B are schematic side views of releasably interlocking elements of a common module and a custom module: A, not interlocked; B, interlocked.
Figure 10B:
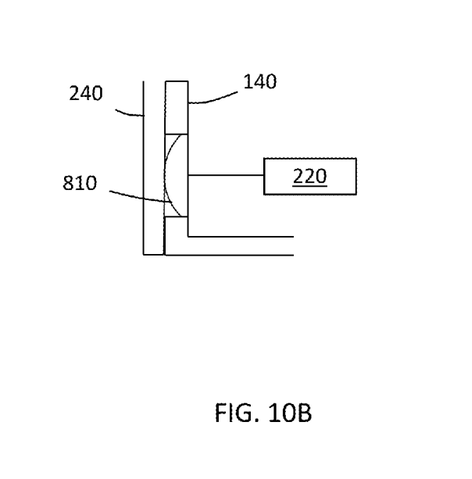
Figure 11A:
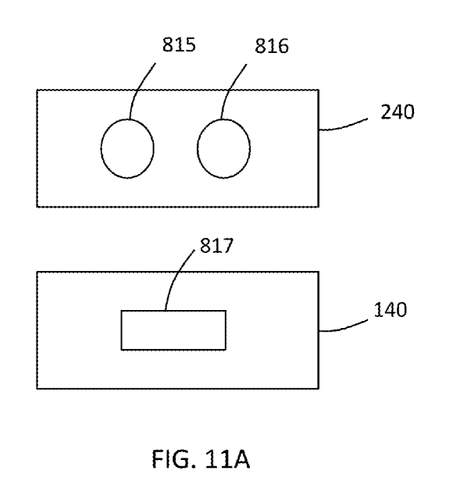
FIGS. 11A-B are schematic views of releasably interlocking elements of a common module and a custom module: A, not interlocked; B, interlocked.
Figure 11B:
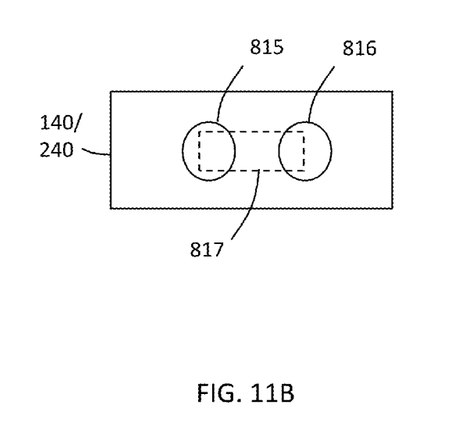

Referring now to FIGS. 9-11, schematic drawings depicting some elements of, for example, a common module and a custom module and interaction of the elements for purposes of ensuring or providing feedback regarding proper alignment are shown.

FIGS. 9A-D depicts schematic front (A, C) and side (B, D) views of interlocking elements, which may be an engagement element 210A or part of housing 240 of custom module or an engagement element 210B or part of housing 140 of common module (see, e.g., FIG. 1). Interlocking element 210A, 240 includes a window or opening 600 through which a portion of protruding element 700 may extend when the elements are interlocked (FIGS. 9C-D). The protruding element 700 may include a tapered or sloped region 710 to facilitate movement of element 210B, 140 towards and engaged position relative to element 210A, 240. The protruding element 700 and area surrounding the opening 600 may be formed of similarly colored material such that, when interlocked, the colors blend to provide visual feedback of proper alignment and interlocking (see, FIG. 9C). Of course, other mechanisms for providing feedback of proper alignment, such as audible feedback (such as clicking into place, etc.), may be used in addition to, or alternatively from, visual feedback.

FIGS. 10A-B are schematic drawings of an electrical feedback mechanism that may be employed to provide feedback of proper alignment and engagement of a custom module and a common module. In the depicted embodiment, an electrical contact apparatus 800 is incorporated into the housing 140 of a common module. The contact apparatus 800 is in electrical communication with control electronics 220, which may be control electronics of the custom module. The contact apparatus 800 includes an activatable element 810 that is configured to be depressable, slidable, etc. to activate a circuit. As the housing 240 of the custom module is moved towards and achieves an engaged position relative to the housing 140 of the common module, the activatable element 810 is depressed, slides, etc. to activate contact apparatus 800 and transmit data to control electronics 240 that proper alignment has been achieved. Control electronics may provide an audible tone, visual display, or the like to indicate proper alignment. Of course, any other suitable mechanism to provide electrical feedback of proper or improper alignment may be used. For example, proper connection of electrical interconnects (e.g., interconnects 120, 27 as shown in FIG. 6) may be used to provide such feedback.

FIGS. 11A-B FIGS. 10A-B are schematic drawings of another embodiment of an electrical feedback mechanism that may be employed to provide feedback of proper alignment and engagement of a custom module and a common module. In the depicted embodiment, electrical contacts 815, 816 are incorporated into, exposed through, disposed on, etc. the housing 240 of the custom module. The contacts 815, 816 are in electrical communication with control electronics (not shown). Another contact 817 is disposed on the housing 140 of the common module. When fully engaged (see FIG. 11B) contact 817 completes a circuit between contacts 815, 816, which allows a signal to be transmitted to the control electronics that proper alignment and engagement has been achieved.

It will be understood that the alignment or engagement feedback mechanisms presented in FIGS. 9-11 are merely for purposes of example and that numerous other mechanisms known in the art may be employed to provide feedback of proper alignment and engagement of a common module relative to a custom module (or alignment or engagement of other modules or components).

Figure 12:
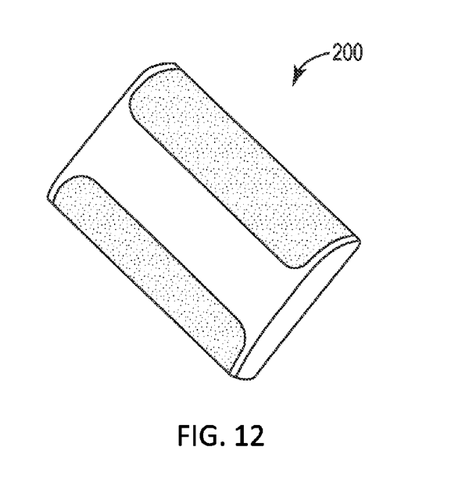
FIGS. 12-14 are schematic diagrams showing various form factors of embodiments of housings of custom modules.
Figure 13:
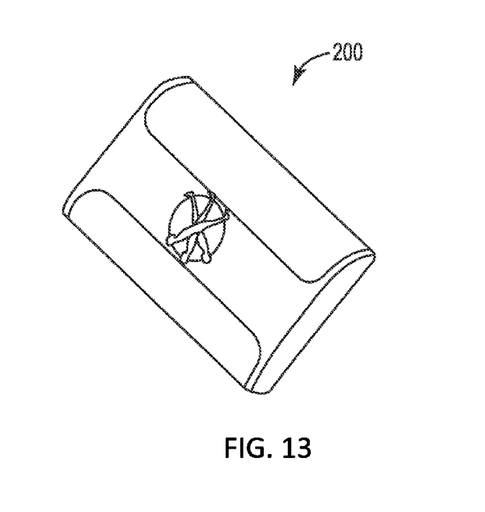
Figure 14:
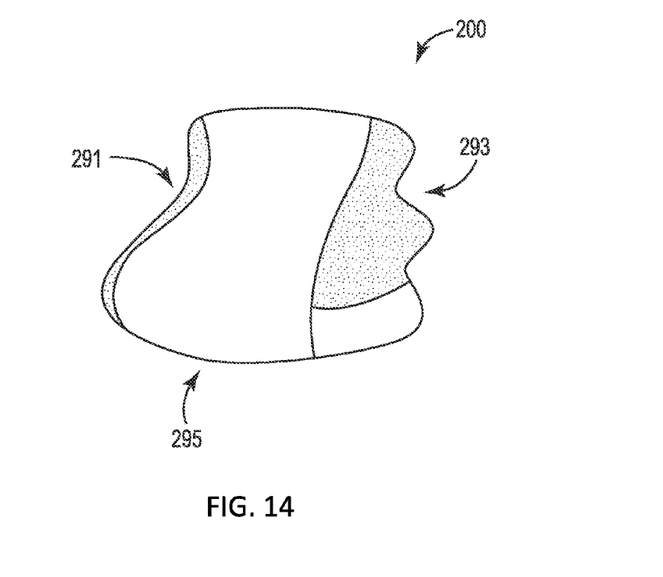

Referring now to FIGS. 12-14 various embodiments of different form factors for custom module 200 are depicted. The form factors may contribute to aesthetics, patient comfort and patient handleability. Accordingly, in addition to customizing therapy through control of pump operation rate and medicament choice, custom module 200 may be customizable for appearance and ergonomic factors. As shown in FIGS. 12-13, housings of custom modules 200 may include design features that a patient may find appealing. Colors, printed patterns or images may be added as desired, with personal preferences ranging from flowers to camouflage, etc. In addition to pleasing appearance, the form factors depicted in FIGS. 12-13 include curved edges for patient comfort as well as grip areas for ease of handling. The form factor depicted in FIG. 14 includes a thumb grip depression 291, finger grip depressions as part of an ergonomic soft grip handle portion 293, as well as a clear top to visualize internal components and verify alignment with common module. It will be understood that the form factor customizations depicted in FIGS. 12-14 present only a small sampling of possible form factors and that a variety of other form factors are contemplated herein.

Figure 15A:
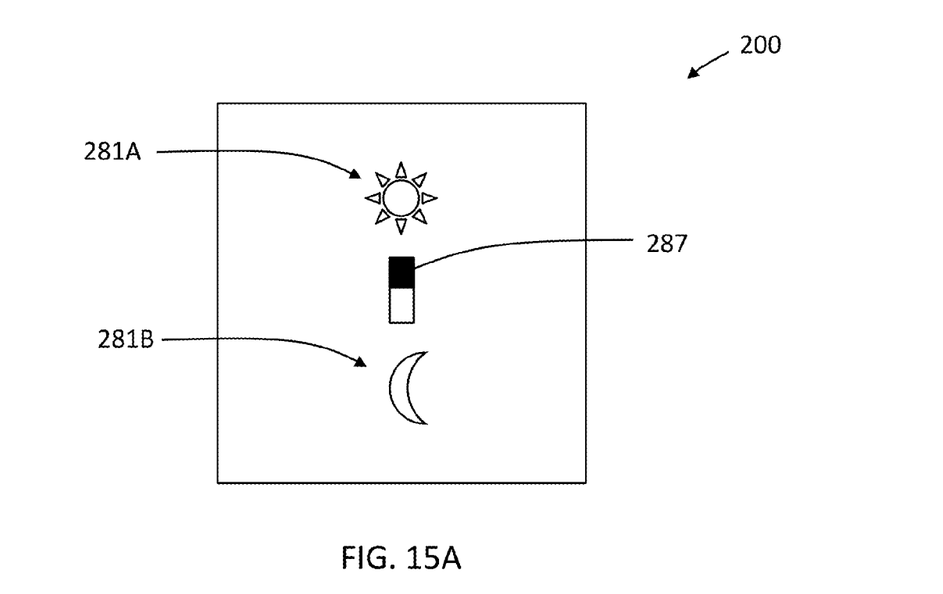
FIGS. 15A-B are schematic drawings of top views of an embodiment of a custom module having a day/night delivery rate switch.
Figure 15B:
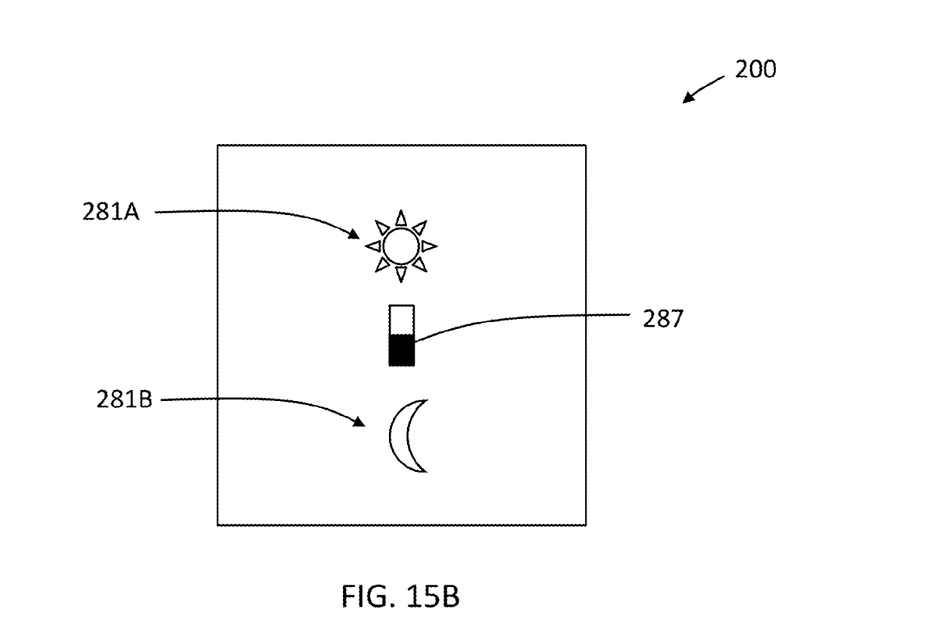

Referring now to FIGS. 15A-B, a schematic drawing of a top view of a custom module 200 is shown. The custom module may include a switch 287 to allow a user to switch the rate at which the infusion device delivers therapeutic agent to a patient. The switch may be a part of control electronics that are operably coupled to the pumping mechanism of the common module. In the depicted embodiment, the switch 287 is configured to allow switching between two rates, such as a day rate and a night rate. The custom module 200 may include indicia such as sun 281A for day rate and moon 281B for night rate to assist the patient in determining how to set the delivery rate. For therapies for which patient initiated switching of rates is not applicable, a custom module without such a delivery rate switch may be employed. Other user control mechanisms appropriate for a given therapy or patient need may be readily incorporated into a custom module. For example, hi/lo, active/rest or any other therapy or patient driven desire for two or more settings may be incorporated. Preferably the switching settings are controllable by a healthcare provider, who can program the device to enable or disable the switching settings.

The methods, systems and devices described herein may be used to deliver any suitable therapy to a patient. In embodiments, injectable ropinirole is delivered via an ambulatory infusion device, such as a patch pump, for treatment of Parkinson's disease. The injectable ropinirole may be an isotonic, citrate-buffered (pH about 4.5), injectable solution that contains 15 mg/ml ropinirole hydrochloride. Such an injectable ropinirole solution may be a solution as described in U.S. patent application Ser. No. 13/828,148, entitled "Injectable Ropinirole Compositions and Methods for Making and Using Same," filed on Mar. 14, 2013, which application is hereby incorporated herein by reference in its entirety to the extent that it does not conflict with the disclosure presented herein.

Thus, embodiments of PERSONALIZED HOUSING FOR AMBULATORY INFUSION DEVICE are disclosed. One skilled in the art will appreciate that the apparatuses, systems and methods described herein can be practiced with embodiments other than those disclosed. The disclosed embodiments are presented for purposes of illustration and not limitation. One will also understand that components of the custom or common modules and associated devices and systems depicted and described with regard to the figures and embodiments herein may be interchangeable.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, "releasably secure" with regard to two components, means that one component may be readily removed and re-attached in the same manner multiple times.

The invention claimed is:

1. An ambulatory infusion device, comprising:
a common module comprising a pump mechanism and a fluid flow path in communication with the pump mechanism; and
a custom module operably coupleable to the common module, the custom module including a (i) reservoir for housing a liquid composition comprising a medicament and (ii) control electronics, wherein the reservoir is configured to fluidly couple with the fluid flow path and the control electronics are configured to electrically couple to the pump mechanism when the common module and the custom module are operably coupled, and wherein, when the common module and the custom module are operably coupled, the pump mechanism is configured to cause the liquid composition from the reservoir to be delivered to a patient via the fluid flow path, and wherein the control electronics are configured to control the rate at which the pump mechanism causes the liquid composition to be delivered.

2. The ambulatory infusion device of claim 1, wherein the control electronics are programmed with instructions to cause the pump mechanism to deliver the liquid composition from the reservoir to the patient at a rate tailored to the patient.

3. The ambulatory infusion device of claim 2, wherein the common module further comprises common module control electronics configured to detect device malfunctions.

4. The ambulatory infusion device of claim 1, wherein the common m further comprises common module control electronics configured to detect device malfunctions.

5. The ambulatory infusion device of claim 1, wherein the custom module comprises housing and the reservoir is releasably securable to the housing.

6. The ambulatory infusion device of claim 1, wherein the custom module comprises a refill port in fluid communication with the reservoir.

7. The ambulatory infusion device of claim 6, wherein the custom module comprises a housing defining an opening for accessing the refill port.

8. The ambulatory infusion device of claim wherein the custom module comprises a housing having a securing element and wherein the common module has a securing feature complementary to the securing element, wherein the securing element and the complementary securing feature cooperate to secure the custom module to the common module.

9. The ambulatory infusion device of claim 1, wherein common module comprises a disposable portion and a reusable portion releasably attachable to the disposable portion, wherein the reuseable portion comprises the pump mechanism and at least a portion of the fluid flow path.

10. The ambulatory infusion device of claim 9, wherein the disposable portion comprises a plate, wherein the reusable portion comprises a housing to which the pumping mechanism is secured, and wherein the plate is configured to releasably attach to the housing of the reusable portion.

11. The ambulatory infusion device of claim 10, wherein the disposable portion further comprises a layer of adhesive disposed on the plate and configured to attach the plate to skin of a patient.

12. The ambulatory infusion device of claim 10, wherein the disposable portion further comprises a fluid interconnect configured to fluidly couple to the portion of the fluid flow fluid pathway of the reusable portion.

13. The ambulatory infusion device of claim 1, wherein the common module comprises a contact apparatus comprising an activatable element configured to be activated when the custom module and the common module are operably coupled and properly aligned, wherein the contact apparatus is operable coupled with the control electronics.

14. The ambulatory infusion device of claim 1, further comprising a layer of adhesive disposed on the common module configured to attach to the skin of the patient, wherein the common module is positioned between the custom module and the layer of adhesive.

15. A custom module for an ambulatory infusion device assembly, comprising:
a housing configured to releasably engage with a common module of the ambulatory device assembly, wherein the common module comprises a pump mechanism and a fluid flow path in communication with the pump mechanism; and
control electronics disposed within the housing and comprising an interconnect configured to electrically couple with an interconnect of the common module when the housing is engaged with the common module, wherein the interconnect of the common module is electrically coupled to the pump mechanism of the common module, and wherein the control electronics are electrically coupled to the pump mechanism when the housing is engaged with the common module and are configured to control the operation rate of the pump mechanism;
a reservoir disposed within the housing; and
a fluid interconnect fluidly coupled with the reservoir, wherein the fluid interconnect is configured to fluidly couple with the fluid flow path of the common module when the housing is engaged with the common module.

16. The custom module of claim 15, wherein the control electronics are programmed with instructions to cause the pump mechanism of the common module to drive the liquid composition from the reservoir to the patient at a rate tailored to the patient when the custom module is coupled to the common module.

17. The custom module of claim 15, wherein the reservoir component comprises a refill port accessible through the housing.

18. The custom module of claim 15, reservoir is releasably securable to the housing.

19. The custom module of claim 15, wherein the housing has a securing element and wherein the common module has a securing feature configured to cooperate with a complementary securing element of the common module to releasably secure the custom module to the common module.

20. The custom module of claim 15, wherein the custom module comprises a disposable portion and a reusable portion releasably attachable to the disposable portion, wherein the reusable portion comprises the control electronics and the disposable portion comprises the reservoir.

* * * * *

UNITED STATES PATENT AND TRADEMARK OFFICE
CERTIFICATE OF CORRECTION

PATENT NO. : 9,707,338 B2  
APPLICATION NO. : 14/063870  
DATED : July 18, 2017  
INVENTOR(S) : Seeley et al.

Page 1 of 1

It is certified that error appears in the above-identified patent and that said Letters Patent is hereby corrected as shown below:

In the Claims

Column 11, Claim 4, Line 22: "common m further" should read --common module further--

Column 11, Claim 8, Line 33: "infusion device of claim wherein" should read --infusion device of claim 1, wherein--

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*